United States Patent [19]

McVannel et al.

[11] Patent Number: 5,206,402

[45] Date of Patent: Apr. 27, 1993

[54] PROCESS FOR PREPARATION OF OMEGA-ALKENYLCHLOROSILANES

[75] Inventors: Donald E. McVannel, Hemlock; Kelly J. Wall, Midland, both of Mich.

[73] Assignee: Dow Corning Corporation, Midland, Mich.

[21] Appl. No.: 946,136

[22] Filed: Sep. 17, 1992

[51] Int. Cl.$^5$ ............................................. C07P 7/08
[52] U.S. Cl. ............................................. 556/479
[58] Field of Search ........................................ 556/479

[56] References Cited

U.S. PATENT DOCUMENTS

| | | | |
|---|---|---|---|
| 2,632,013 | 3/1953 | Wagner | 260/448.2 |
| 2,637,738 | 5/1953 | Wagner | 260/448.2 |
| 2,721,973 | 10/1955 | MacKenzie et al. | 556/479 |
| 2,851,473 | 9/1958 | Wagner | 260/448.2 |
| 3,159,662 | 12/1964 | Ashby | 260/448.2 |
| 5,041,595 | 8/1991 | Young et al. | 556/479 |

FOREIGN PATENT DOCUMENTS 1104206 2/1968 United Kingdom.
1526324 9/1978 United Kingdom.

*Primary Examiner*—Paul F. Shaver
*Attorney, Agent, or Firm*—William F. Boley

[57] ABSTRACT

The present invention is a process for the preparation of omega-alkenylchlorosilanes. The process comprises reacting a mixture comprising an $\alpha,\Omega$-diene and an organohydrosilane in the presence of a supported platinum catalyst to form an $\Omega$-alkenylchlorosilane, where the mole ratio of the $\alpha,\Omega$-diene to the organohydrosilane is within a range of about 6:1 to 50:1. A preferred process is run as a continuous process employing a fixed-bed of silica gel supported platinum catalyst and excess $\alpha,\Omega$-diene is recovered and recycled to the process.

34 Claims, No Drawings

PROCESS FOR PREPARATION OF OMEGA-ALKENYLCHLOROSILANES

BACKGROUND OF INVENTION

The present invention is a process for the preparation of omega-alkenylchlorosilanes. The process comprises reacting a mixture comprising an alpha,omega-diene ($\alpha,\Omega$-diene) and an organohydrosilane in the presence of a supported platinum catalyst to form an $\Omega$-alkenylchlorosilane, where the mole ratio of the $\alpha,\Omega$-diene to the organohydrosilane is within a range of about 6:1 to 50:1. A preferred process is run as a continuous process employing a fixed-bed of silica gel supported platinum catalyst and excess $\alpha,\Omega$-diene is recovered and recycled to the process.

Addition reactions between compounds containing silicon-hydrogen linkages and compounds containing aliphatic unsaturation, typically referred to as hydrosilylation or hydrosilation reactions, are well known in the art and provide a means of forming a wide variety of products. These addition reactions can be employed to form monomeric materials or polymeric materials which are useful, respectively, as intermediates in the preparation of more complicated products and which are useful as coating materials, elastomers, and insulating materials.

Of particular importance to the coatings industry is the use of the hydrosilylation reaction to react an organohalosilane containing at least one hydrogen with a $\alpha,\Omega$-dienes to form organohalosilanes having silicon-bonded groups containing olefinic unsaturation. Typically during the hydrosilyation reaction some isomerization of the diene occurs resulting in migration of the unsaturated bond from a terminal to an internal position in the desired silicon-bonded group. Products having such internal unsaturation exhibit low reactivity with respect to further hydrosilylation to produce surface coatings, elastomers, and other products, and thus represent an undesirable component of the reaction product.

Unexpectedly, the present inventors have discovered that migration of the unsaturated bond from a terminal to an internal position in the desired silicon-bonded group can be reduced in the presence of a supported platinum catalyst by controlling the mole ratio of the $\alpha,\Omega$-diene to organohydrosilane within a range of about 6:1 to 50:1. The low levels of unsaturated bond migration in the described process, allows the process to be run as a continuous process with recovery and recycling of excess $\alpha,\Omega$-diene. At mole ratios of $\alpha,\Omega$-diene to organohydrosilane below about 6:1, unsaturation bond migration in the $\alpha,\Omega$-diene makes recycling of the $\alpha,\Omega$-diene inefficient because of incorporation of an excessive accumulation of diene having an internal unsaturated bond in the alkenylchlorosilane product.

Therefore, an objective of the present invention is to provide a process where there is a reduction in the migration of terminal unsaturated bonds to an internal position within a diene. A further objective of the present invention is to provide a process where excess diene employed in the process can be recovered and recycled to the process while maintaining a high levels of the desired $\Omega$-alkenylchlorosilane product.

The use of a platinum complex to catalyze the reaction between a compound containing aliphatic unsaturation and a compound containing a silicon-hydrogen bond is well known and has been described, for example, in British patent No. 1,104,206, Pub. Feb. 21, 1968, and by Ashby in U.S. Pat. No. 3,159,662, issued Dec. 1, 1964.

The use of a supported platinum catalyst to catalyze the reaction between a compound containing aliphatic unsaturation and a compound containing a silicon-hydrogen bond has also been described. Wagner, U.S. Pat. No. 2,632,013, issued Mar. 17, 1953, describes a process for reacting an unsaturated hydrocarbon with any compound containing one or more silicon-hydrogen bonds in its molecule. Wagner teaches that the hydrocarbon may have one or more unsaturated bonds. Wagner further teaches that the process can be facilitated by catalysts such as platinum metals, platinum black, platinized silica gel, and platinized asbestos. In the only example of the reactivity of a diene provided by Wagner, it is reported that butadiene reacts with trichlorosilane to produce the two cyclic compounds beta-cyclohexenylethyltrichlorosilane and betatrichlorosilylethylcyclohexyltrichlorosilane. The mole ratio of reactants is not provided.

Wagner, U.S. Pat. No. 2,637,738, issued May 5, 1953, describes a platinum supported on finely-divided charcoal that selectively promotes the 1,2-addition of the siliconhydrogen bond across a pair of aliphatic carbon atoms linked by multiple bonds. In this patent, Wagner provides an example where two moles of butadiene is reacted with two moles of trichlorosilane in the presence of the platinum on charcoal catalyst. The major products of this reaction were reported to be butenyl trichlorosilane i.e. ($CH_3CH=CH_2SiCl_3$) and bis(trichlorosilyl) butane i.e. $CH_3CH(SiCl_3)CH_2CH_2SiCl_3$.

Wagner, U.S. Pat. No. 2,851,473, issued Sept. 9, 1958, describes a platinum deposited on the gamma allotrope of alumina as a catalyst for the reaction between compounds containing silicon-hydrogen linkages and compounds containing aliphatic unsaturation. No examples or guidance is given as to the use of the platinum-/alumina catalyst with dienes.

British patent No. 1,526,324, Pub. Sep. 27, 1978, describes a group of hydrosilylation catalysts formed by reacting an inorganic solid containing surface hydroxyl groups and aminoorganosiloxy groups with certain platinum compounds.

The type catalysts reported in this patent are representative of the preferred type catalysts in the present process and incorporated by reference herein. However, British patent No. 1,526,324 provides no examples or guidance as to the use of the described platinum catalysts with dienes.

Based upon the cited art, surprisingly, the inventors have found that in a supported platinum catalyzed process for reacting an $\alpha,\Omega$-diene with a organohydrosilane, reduction of migration of the terminal unsaturated bonds into the internal of the diene can be reduced by running the process where the mole ratio of the $\alpha,\Omega$-diene to organohydrosilane is within a range of about 6:1 to 50:1. This allows for higher yields of the desired $\Omega$-alkenylchlorosilanes and allows for excess $\alpha,\Omega$-diene present in the process to be recovered and reused in the process while maintaining acceptable yields of the desired $\Omega$-alkenylchlorosilanes.

SUMMARY OF INVENTION

The present invention is a process for the preparation of omega-alkenylchlorosilanes. The process comprises reacting a mixture comprising an $\alpha,\Omega$-diene and an organohydrosilane in the presence of a supported platinum catalyst to form an Ω-alkenylchlorosilane, where the mole ratio of the α,Ω-diene to the organohydrosilane is within a range of about 6:1 to 50:1. A preferred process is run as a continuous process employing a fixed-bed of silica gel supported platinum catalyst and excess α,Ω-diene is recovered and recycled to the process.

DESCRIPTION OF INVENTION

The present invention is a process for preparing Ω-alkenylchlorosilanes. The process comprises:

(A) contacting a mixture comprising an organohydrosilane described by formula

$$R_aHSiCl_{3-a} \qquad (1)$$

and an α,Ω-diene comprising five to 14 carbon atoms, where the mole ratio of the α,Ω-diene to the organohydrosilane is within a range of about 6:1 to 50:1, with a supported platinum catalyst at a temperature within a range of about 10° C. to 100° C., and (B) recovering an Ω-alkenylchlorosilane described by formula

$$R_aR^1SiCl_{3-a} \qquad (2)$$

where each R is independently selected from a group consisting of alkyls comprising one to six carbon atoms, $R^1$ is selected from a group consisting of Ω-alkenyls comprising five to 14 carbon atoms, and a=0, 1, or 2.

The present process can be run as a batch, semi-batch, or continuous process. The process can be run in any standard type reactor suitable for contacting chlorosilanes with a supported catalyst. The process can be run, for example, in a continuous-stirred tank reactor, a fixed-bed reactor, or a fluidized-bed reactor. Preferred is when the process is run as a continuous process in a fixed-bed reactor. Most preferred is when the present process is run as a continuous process in a plug-flow mode.

A mixture comprising an organohydrosilane and an α,Ω-diene is provided to the reactor. The mixture may be preformed and fed to the reactor or each component may be fed separately to the reactor with the mixture being formed therein.

The organohydrosilanes useful in the present invention are described by formula (1). The organohydrosilanes can have zero, one, or two substituents R, where each R is independently selected from a group consisting of alkyls comprising one to six carbon atoms. The substituent R can be, for example, methyl, ethyl, propyl, butyl, iso-butyl, tert-butyl, pentyl, or hexyl. Preferred is when R is methyl. The organohydrosilanes must contain a hydrogen bonded to silicon and can contain one, two, or three chlorine atoms. The preferred organohydrosilanes are selected from a group consisting of methyldichlorosilane and dimethylchlorosilane.

The α,Ω-diene comprises five to 14 carbons. The α,Ω-diene can be, for example, 1,4-pentadiene, 1,5-hexadiene, 1,9-decadiene, and 1,13-tetradecadiene. The preferred α,Ω-diene is 1,5-hexadiene.

The inventors have discovered that when the mole ratio of the α,Ω-diene to the organohydrosilane is within a range of about 6:1 to 50:1 isomerization of the α,Ω-diene to isomers having internal unsaturated bonds is reduced in comparison to when lower ratios are employed. The result of this discovery is that improved yields of Ω-alkenylchlorosilanes can be obtained from the process. Preferred is when the mole ratio of the α,Ω-diene to the organohydrosilane is within a range of about 10:1 to 30:1. Even more preferred is when the mole ratio of the α,Ω-diene to the organohydrosilane is within a range of about 12:1 to 25:1.

Also, because of the reduced isomerization of the α,Ω-diene it is possible to recover and recycle unreacted α,Ω-diene to the process while still maintaining acceptable yields of the Ω-alkenylchlorosilanes. Therefore, in a preferred process unreacted α,Ω-diene from the process is recovered and recycled to the process. The unreacted α,Ω-diene can be recovered by standard means, for example, distilling the final product mixture containing the Ω-alkenylchlorosilanes and the α,Ω-diene to separate the mixture into an Ω-alkenylchlorosilane containing fraction and an α,Ω-diene containing fraction.

The process is conducted at a temperature within a range of about 10° C. to 100° C. The process may be conducted at temperature lower than about 10° C., but depending upon the reactants the process may be unacceptably slow. The process may be conducted at temperature above about 100° C., however at higher temperatures isomerization of the α,Ω-diene may occur at an unacceptable level. A preferred temperature is within a range of about 20° C. to 50° C.

It is preferred that the present process be run at a pressure which insures the organohydrosilane and α,Ω-diene are kept in a liquid state. The required pressure will depend upon both the chemical formula of the reactants and the temperature at which the process is run. Generally, a suitable pressure will be found within a range of about zero psig to 100 psig.

The mixture comprising the organohydrosilane and the α,Ω-diene is contacted with a supported platinum catalyst. The solid support material can be any solid relatively inert material of appropriate size and with the ability to retain the platinum catalyst. The platinum catalyst may be retained by the support material by standard means, for example, adsorption, ionic bonding, covalent bonding, or physical entrapment. The support material may be, for example, carbon, activated carbon, graphite, silica, silica-gel, alumina, alumina-silica, and diatomaceous earth. A preferred support material is selected from a group consisting of silica-gel and carbon. The most preferred support material is silica-gel. The support material can be in the form of particles, powders, flakes, chips, chunks, and pellets.

The size of the support material is not critical to the present invention. In general, support materials with diameters within a range of about 15μ to 10 mm are considered useful. The lower size limit is determined principally by the ability to handle and recover the supported platinum catalyst and the acceptable pressure drop across a fixed-bed, when a fixed-bed reactor is employed. The upper size limit is determined principally by the ability to provide sufficient surface bound platinum catalyst for the process to run at an econimically reasonable rate. A preferred diameter for the solid support material is within a range of 1 mm to 5 mm.

The weight of platinum catalyst retained on the support material can be within a range of about 0.01 to 50 weight percent platinum. Preferred is when the weight of platinum catalyst retained on the support material is within a range of about 0.1 to 5.0 weight percent platinum. The weight percent of platinum on the solid support material is calculated as the weight of platinum atoms retained by the support material divided by the weight of the support material, the quotient multiplied by 100.

An effective concentration of platinum catalyst in the present process is where the weight of platinum atoms is about 0.0001 to 0.5 percent of the combined weight of the $\alpha,\Omega$-diene and organohydrosilane added to the process. Preferred is where the concentration of platinum atoms is about 0.001 to 0.1 weight percent of the combined weight of the $\alpha,\Omega$-diene and organohydrosilane added to the process.

The platinum may be bound to the support as platinum metal (Pt°) or as a platinum compound. The platinum compound may be, for example, $PtCl_2$, $H_2PtCl_6$, $Na_2PtCl_4 \cdot 4H_2O$, $K\{Pt(CH_2\!\!=\!\!CH_2)Cl_3\}H_2O$, $Pt_2(CH_2\!\!=\!\!CH_2)_2Cl_4$, $Cl_2Pt(Et_2S)_2$ in which Et=ethyl, $\{PtCl_2P(C_6H_5)_3\}_2$, $PtCl_2\{P(C_6H_5)_3\}_2$ and $PtBr_2(NH_3)_2$.

A preferred supported platinum catalyst for use in the present process is a bound silyl/platinum complex prepared by reacting (i) an inorganic solid having surface reactive groups; (ii) an organosilicon compound described by the general formula

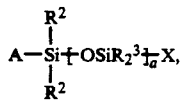

where A represent an atom or group which is reactive with the surface groups in (i), each $R^2$ is independently selected from a group consisting of a chlorine atom, a bromine atom, a monovalent hydrocarbon group comprising from one to six carbon atoms, an alkoxy group comprising from one to 6 carbon atoms, and an oxime group comprising less than 14 carbon atoms, each $R^3$ is an independently selected monovalent hydrocarbon group having from one to eight carbon atoms, X is a monovalent group attached to silicon through a silicon to carbon bond having up to 11 carbon atoms and comprising carbon, hydrogen, and optionally oxygen, there also being present in X at least one sulphur or nitrogen atom, and a is an integer from 1 to 20; and (iii) a platinum compound or complex described by the formula $PtL_b$ where each L is a ligand at least one of which is displaceable by amino or mercapto and b is a number such that the free valencies of platinum are satisfied.

In the general formula for the organosilicon compound (ii) of the silyl/platinum complex, the substituent A may be any atom or group which is reactive with the support material. The substituent A may be for example chlorine; bromine; alkoxy such as methoxy, ethoxy, propoxy, butoxy, ethoxyethoxy; hydroxyl; and oxime. Each of the $R^2$ substituents may be of the same type as those exemplified for A but may also be selected from alkyl, aryl, aralkyl, alkaryl and halogenated alkyl. Preferably A represents an alkoxy group having from one to four carbon atoms e.g. methoxy or ethoxy and $R^2$ is methyl, phenyl or an alkoxy group having from one to four carbon atoms.

Each substituent $R^3$, when present in the silyl/platinum complex, may be, for example, methyl, ethyl, propyl, hexyl, or phenyl. The group X is a monovalent group attached to silicon by a silicon to carbon linkage and having at least one sulphur or nitrogen atom. Specific examples of X groups are $-(CH_2)_3SH$, $-(CH_2)_4SH$, $-CH_2CHCH_3CH_2S(C_6H_4)$, $-(CH_2)_3NH_2$, $-(CH_2)_4NHCH_3$, $-CH_2CHCH_3CH_2NHCH_2CH_2NH_2$, $-CH_2CHCH_3CH_2N(C_3H_7)_2$, $-(CH_2)_3NHCH_2CH_2NH_2$, and $-(CH_2)_4NH(CH_2)_4NH_2$. Preferably X is selected from a group consisting of $-(CH_2)_3NH_2$, $-(CH_2)_3NHCH_2CH_2NH_2$, and $-CH_2CHCH_3CH_2NHCH_2CH_2NH_2$.

The ligand L may be an alkyl, for example methyl, butyl, or hexyl; phenyl; —CO; a halide, for example, chlorine; hydrogen; acac; amino; or an olefin, for example, ethylene. Examples of platinum compounds useful in the present useful in the silyl/platinum complex are $PtCl_2$, $H_2PtCl_6$, $Na_2PtCl_4 \cdot 4H_2O$, $K\{Pt(CH_2\!\!=\!\!CH_2)Cl_3\}H_2O$, $Pt_2(CH_2\!\!=\!\!CH_2)_2Cl_4$, $Cl_2Pt(Et_2S)_2$ in which Et=ethyl, $\{PtCl_2P(C_6H_5)_3\}_2$, $PtCl_2\{P(C_6H_5)_3\}_2$ and $PtBr_2(NH_3)_2$.

When the supported platinum catalyst employs a silyl/platinum complex, silica gel is the preferred support material. More preferred is a bound silyl/platinum complex where silica gel is the support material and the supported platinum catalyst is heat activated by heating at a temperature within a range of about 60° C. to 150° C. for a period of time within a range of about 0.5 to 6.0 hours. The most preferred supported platinum catalyst for the present process is one employing a bound silyl/platinum complex described by formula $\equiv SiCH_2CH_2CH_2N{:}PtCl_2$ where the remaining three bonds of the silicon atom are bounded through oxygen linkages to silica gel and the supported platinum catalyst is heat activated as previously described.

Examples of bound silyl/platinum complex catalyst and method for their preparation are described in British Patent No. 1,526,324, Pub. Sep. 27, 1978, which is hereby incorporated by reference into this specification.

An $\Omega$-alkenylchlorosilane as described by formula (2) is recovered from the process. The $\Omega$-alkenylchlorosilane has zero, one, or two substituents R, where R is as previously described. The $\Omega$-alkenylchlorosilane has one, two, or three chlorine atoms. The $\Omega$-alkenylchorosilane has substituent $R^1$, where $R^1$ is selected from a group consisting of $\Omega$-alkenyl radicals comprising five to 14 carbon atoms. The $\Omega$-alkenyl radical can be, for example, 4-pentenyl, 5-hexenyl, or 9-decenyl. Preferred $\Omega$-alkenylchlorosilanes to be prepared by the present process are selected from the group consisting of 5-hexenylmethyldichlorosilane, 5-hexenyldimethylchlorosilane, and 5-hexenyltrichlorosilane.

Recovery of the $\Omega$-alkenylchlorosilane can be effected by standard means. For example, when required, filtration may be employed to separate supported platinum catalyst from the $\Omega$-alkenylchlorosilane. When desired, the liquid mixture comprising the $\Omega$-alkenylchlorosilane can be separated by, for example, distillation or thin film vaporization to recover a mixture enriched in the $\Omega$-alkenylchlorosilanes. Alternatively, the liquid mixture comprising the $\Omega$-alkenylchlorosilane may be stored or used without further treatment, after separation from the supported platinum catalyst.

The following examples are provide to illustrate the present invention. These examples are not intended to limit the scope of the present claims.

EXAMPLE 1

The effect of the mole ratio of hexadiene to methyldichlorosilane on the isomerization of hexadiene in the presence of a silica gel supported platinum catalyst was evaluted. The reactor consisted of a water-cooled stainless steel cylinder providing for a catalyst bed about 2.5 cm in diameter and 30 cm long. The catalyst was prepared by adding 45 g of $(EtO)_3Si(CH_2)_3NH_2$ to 1000 g of water and adding this mixture to 300 g of Grace grade 57 silica gel (W. R. Grace and Co., Baltimore, MD). The silica gel was mixed with the silane for one hour at ambient temperature. The treated silica gel was then washed with water and excess water drained off. About 31.7 g of $Na_2PtCl_4$, as a five weight percent platinum in water solution, was added to 1500 mL of a 33% methanol in water solution. This platinum containing solution was then added to the treated silica gel and mixed for about 16 hours at ambient temperature. The resultant silica gel supported platinum catalyst was washed with distilled water, then with methanol, and dried under vacuum (5 mm Hg) at about 60° C. for 25 hours. The silica gel supported platinum catalyst was calculated to have a theoretical platinum content of about 0.5 weight percent.

A packed bed of the catalyst was formed in the reactor described above. For purpose of comparison and not within the scope of the present claims, hexadiene and methyldichlorosilane were fed to the reactor at a ratio of three moles of hexadiene per mole of methyldichlorosilane. In a second run, hexadiene and methyldichlorosilane were fed to the reactor at a ratio of 25 moles of hexadiene per mole of methyldichlorosilane. During both runs the temperature of the reactor was kept at about 25° C. and the feed rate of reactants to the reactor was metered to provide a calculated residence time for reactants in the reactor of about 30 minutes. In the first run, where the ratio of hexadiene to methyldichlorosilane was 3:1, the hexadiene was fed to the reactor at a rate of 7 mL/Min. and the methyldichlorosilane at a rate of 2.0 mL/Min. In the second run, where the ratio of hexadiene to methyldichlorosilane was 25:1, the hexadiene was fed to the reactor at a rate of about 26 mL/Min. and the methyldichlorosilane at a rate of about 0.9 mL/Min. The pressure of the reactor was kept at about 80 psig.

The liquid mixture exiting the reactor was distilled at about 165° C. to provide an overhead fraction containing primarily hexadiene and a bottom fraction containing primarily alkenylmethyldichlorosilane. The bottom fraction was analyzed by gas chromatography using a mass spectrometer as a detector (GC/MS) and the weight percent of 5-alkenylmethyldichlorosilane (5-Alkenyl) and 4-alkenylmethyldichlorosilane (4-Alkenyl) determined. The results are presented in Table 1. The results are expressed as the mean value for four runs plus or minus the standard deviation.

TABLE 1

Effect of Mole Ratio of Hexadiene to Methyldichlorosilane on Isomerization of Hexadiene in The Presence of a Silica Gel Supported Platinum Catalyst

| Diene:Silane Mole Ratio | 5-Alkenyl Wt % | 4-Alkenyl Wt % |
|---|---|---|
| 3:1 | 91.62 ± 0.95 | 8.38 ± 0.95 |
| 25:1 | 98.56 ± 0.39 | 1.44 ± 0.39 |

Example 2.

The effect of the mole ratio of hexadiene to methyldichlorosilane on the isomerization of hexadiene in the presence of a carbon support platinum catalyst was evaluated. The process was conducted similar to that described in Example 1. The carbon supported catalyst comprised 0.5 weight percent platinum on carbon chips and was obtained from Englehard Industries, Newark, NJ. The liquid exiting the reactor was distilled at about 165° C. and analyzed by GC/MS as described in Example 1. The results are reported in Table 2. The headings of Table 2 are as previously described for Example 1.

TABLE 2

Effect of Mole Ratio of Hexadiene to Methyldichlorosilane on Isomerization of Hexadiene in The Presence of a Carbon Supported Platinum Catalyst

| Diene:Silane Mole Ratio | 5-Alkenyl Wt % | 4-Alkenyl Wt % |
|---|---|---|
| 3:1 | 89.86 ± 1.72 | 10.14 ± 1.72 |
| 25:1 | 94.60 ± 0.88 | 5.40 ± 0.88 |

We claim:

1. A process for preparing Ω-alkenylchlorosilanes, the process comprising:
   (A) contacting a mixture comprising an organohydrosilane described by formula $R_aHSiCl_{3-a}$ 

and an α,Ω-diene comprising five to 14 carbon atoms, where the mole ratio of the α,Ω-diene to the organohydrosilane is within a range of about 6:1 to 50:1, with a supported platinum catalyst at a temperature within a range of about 10° C. to 100° C., and
   (B) recovering an Ω-alkenylchlorosilane described by formula
   $R_aR^1SiCl_{3-a}$ 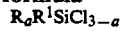

where each R is independently selected from a group consisting of alkyls comprising one to six carbon atoms, $R^1$ is selected from a group consisting of Ω-alkenyls comprising five to 14 carbon atoms, and a=0, 1, or 2.

2. A process according to claim 1, where excess α,Ω-diene present in the process is recovered and recycled to the process.

3. A process according to claim 1, where the process is run as a continuous process employing a fixed-bed of the supported platinum catalyst.

4. A process according to claim 3, where the process is run in a plug-flow mode.

5. A process according to claim 1, where R is methyl.

6. A process according to claim 1, where the organohydrosilane is selected from a group consisting of methyldichlorosilane and dimethylchlorosilane.

7. A process according to claim 1, where the α, Ω-diene is 1,5-hexadiene.

8. A process according to claim 1, where the mole ratio of the α, Ω-diene to the organohydrosilane is within a range of about 12:1 to 25:1.

9. A process according to claim 1, where the temperature is within a range of about 20° C. to 50° C.

10. A process according to claim 1, where the process is run at a pressure which insures the α, Ω-diene and the organohydrosilane are in a liquid state.

11. A process according to claim 1, where the platinum is supported on a solid support material selected from a group consisting of silica-gel and carbon.

12. A process according to claim 11, where the platinum is supported on silica-gel.

13. A process according to claim 1, where the supported platinum catalyst comprises about 0.1 to 5.0 weight percent platinum supported on a support material.

14. A process according to claim 1, where the supported platinum catalyst provides a concentration of platinum within a range of about 0.001 to 0.1 weight percent of the α, Ω-diene and organohydrosilane added to the process.

15. A process according to claim 1, where the Ω-alkenylchlorosilane is selected from a group consisting of 5-hexenylmethyldichlorosilane, 5-hexenyldimethylchlorosilane, and 5-hexenyltrichlorosilane.

16. A process according to claim 1, where the organohydrosilane is selected from a group consisting of methyldichlorosilane and dimethylchlorosilane, the α, Ω-diene is 1,5-hexadiene, the mole ratio of the α, Ω-diene to the organohydrosilane is within a range of about 12:1 to 25:1, the support for the supported platinum catalyst is selected from a group consisting of silica-gel and carbon, the supported platinum catalyst provides a concentration of platinum within a range of about 0.001 to 0.1 weight percent of the α, Ω-diene and organohydrosilane added to the process, the temperature is within a range of about 20° C. to 50° C., the process is run at a pressure which insures the α, Ω-diene and the organohydrosilane are in a liquid state, and excess α, Ω-diene present in the process is recovered and recycled to the process.

17. A process according to claim 1, were the supported platinum catalyst is a bound silyl/platinum complex prepared by reacting (i) an inorganic solid having surface reactive groups; (ii) an organosilicon compound described by the general formula

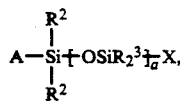

$$A-\underset{\underset{R^2}{|}}{\overset{\overset{R^2}{|}}{Si}}\text{(OSiR}_2^3\text{)}_{\overline{a}}X,$$

where A represent an atom or group which is reactive with the surface groups in (i), each $R^2$ is independently selected from a group consisting of a chlorine atom, a bromine atom, a monovalent hydrocarbon group comprising from one to six carbon atoms, an alkoxy group comprising from one to six carbon atoms, and an oxime group comprising less than 14 carbon atoms, each $R^3$ is an independently selected monovalent hydrocarbon group comprising from one to eight carbon atoms, X is a monovalent group attached to silicon through a silicon to carbon bond having up to 11 carbon atoms and comprising carbon, hydrogen, and optionally oxygen, there also being present in X at least one sulphur or nitrogen atom, and a is an integer from one to 20; and (iii) a platinum compound described by the formula $PtL_b$, where each L is a ligand at least one of which is displaceable by amino or mercapto and b is a number such that the free valencies of platinum are satisfied.

18. A process according to claim 17, where A is an alkoxy radical comprising from one to four carbon atoms.

19. A process according to claim 18, where A is selected from a group consisting of methoxy and ethoxy.

20. A process according to claim 17, where each $R^2$ is independently selected from a group consisting of methyl, phenyl, and alkoxys comprising from one to four carbon atoms.

21. A process according to claim 17, where each $R^3$ is methyl.

22. A process according to claim 17, where X is selected from a group consisting of —(CH$_2$)$_3$NH$_2$, —(CH$_2$)$_3$NHCH$_2$CH$_2$NH$_2$, and —CH$_2$CHCH$_3$CH$_2$NHCH$_2$CH$_2$NH$_2$.

23. A process according to claim 17, where the inorganic solid having surface reactive groups is silica-gel.

24. A process according to claim 17, where the supported platinum catalyst is heat activated by heating at a temperature within a range of about 60° C. to 150° C. for a period of time within a range of about 0.5 to 6.0 hours.

25. A process according to claim 17, where the supported platinum catalyst provides a concentration of platinum within a range of about 0.001 to 0.1 weight percent of the α,Ω-diene and organohydrosilane added to the process.

26. A process according to claim 17, where the mole ratio of the α,Ω-diene to the organohydrosilane is within a range of about 12:1 to 25:1.

27. A process according to claim 17, where the silyl/platinum complex is described by formula ≡SiCH$_2$CH$_2$CH$_2$N:PtCl$_2$, and the remaining three bonds of the silicon atom are bonded through oxygen linkages to silica-gel.

28. A process according to claim 27, where the supported platinum catalyst is heat activated by heating at a temperature within a range of about 60° C. to 150° C. for a period of time within a range of about 0.5 to 6.0 hours.

29. A process according to claim 28, where the process is run as a continuous process employing a fixed-bed of the supported platinum catalyst.

30. A process according to claim 29, where excess α,Ω-diene present in the process is recovered and recycled to the process.

31. A process according to claim 29, where the process is run in a plug-flow mode.

32. A process according to claim 17, where the Ω-alkenylchlorosilane is selected from a group consisting of 5-hexenylmethyldichlorosilane, 5-hexenyldimethylchlorosilane, and 5-hexenyltrichlorosilane.

33. A process according to claim 17, where the organohydrosilane is selected from a group consisting of methyldichlorosilane and dimethylchlorosilane, the α,Ω-diene is 1,5-hexadiene, the mole ratio of the α, Ω-diene to the organohydrosilane is within a range of about 12:1 to 25:1, the supported platinum catalyst provides a concentration of platinum within a range of about 0.001 to 0.1 weight percent of the α,Ω-diene and organohydrosilane added to the process, the temperature is within a range of about 20° C. to 50° C., the process is run at a pressure which insures the α,Ω-diene and the organohydrosilane are kept in a liquid state, and excess α,Ω-diene present in the process is recovered and recycled to the process.

34. A process according to claim 33, where the silyl/platinum complex is described by formula ≡SiCH$_2$CH$_2$CH$_2$N:PtCl$_2$, and the remaining three bonds of the silicon atom are bonded through oxygen linkages to silica-gel.

* * * * *